(12) United States Patent
Atchley et al.

(10) Patent No.: US 8,455,184 B2
(45) Date of Patent: Jun. 4, 2013

(54) DIFFERENTIAL MULTIPLEXING WITH PATTERN RECOGNITION

(75) Inventors: Daniel H. Atchley, USAF Academy, CO (US); Craig T. Narasaki, Colorado Springs, CO (US); John R. Hickman, Helotes, TX (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 1496 days.

(21) Appl. No.: 11/786,260

(22) Filed: Apr. 11, 2007

(65) Prior Publication Data

US 2012/0122704 A1    May 17, 2012

Related U.S. Application Data

(60) Provisional application No. 60/792,804, filed on Apr. 18, 2006.

(51) Int. Cl.
| | |
|---|---|
| *C12Q 1/00* | (2006.01) |
| *C12Q 1/68* | (2006.01) |
| *G01N 33/53* | (2006.01) |
| *G01N 33/567* | (2006.01) |
| *C07H 19/00* | (2006.01) |
| *C07H 21/04* | (2006.01) |

(52) U.S. Cl.
USPC ............. 435/4; 435/6.1; 435/6.11; 435/6.12; 435/7.1; 435/7.2; 536/22.1; 536/24.32

(58) Field of Classification Search
None
See application file for complete search history.

(56) References Cited

U.S. PATENT DOCUMENTS

2003/0027135 A1*  2/2003  Ecker et al. ............... 435/6

OTHER PUBLICATIONS

Houf et al. FEMS Microbiology Letters. 2000. 193:89-94.*
Mehrotra et al. Journal of Clinical Microbiology. 2000 38(3): 1032-1035.*
Morin et al. Clinical Chemistry. 2004. 50(11): 2037-2044.*
Bradford. Cytometry Para A 61A: 142-152 (2004).*
Alamo. Cytometry (Communications in Clinical Cytometry) 42: 363-370 (2000).*
Diekema, et al., Rapid Detection of Antimicrobial-Resistant Organism Carriage: an Unmet Clinical Need, Journal of Clinical Microbiology, Jul. 2004, p. 2879-2883 vol. 42, No. 7.
Elnifro, et al., Multiplex PCR: Optimization and Application in Diagnostic Virology, Clinical Microbiology Reviews, Oct. 2000, p. 559-570 vol. 13, No. 4.

(Continued)

*Primary Examiner* — Robert T Crow
*Assistant Examiner* — Joseph G Dauner
(74) *Attorney, Agent, or Firm* — AFMCLC/JAZ; Rebecca Greendyke; Paul Heydon

(57) ABSTRACT

This novel form of multiplexing allows the user to probe for multiple targets and simultaneously identify a specific target. An example of solutions provided here comprises: providing one or more assay mixes for a number of targets (the number of assay mixes is less than the number of targets); providing a number of reference patterns (each of the reference patterns is associated with one of the targets); contacting each of a number of aliquots with one of the assay mixes; generating a result pattern, based on positive or negative results; and selecting the reference pattern most similar to the result pattern, to thereby detect the target. Differential multiplexing with pattern recognition may involve molecular or immunological techniques to identify one of many indicators of drug use, illness, disease, or medical condition.

17 Claims, 1 Drawing Sheet

OTHER PUBLICATIONS

Fukushima, et al., Duplex Real-Time SYBR Green PCR Assays for Detection of 17 Species of Food- or Waterborne Pathogens in Stools, Journal of Clinical Microbiology, Nov. 2003, p. 5134-5146 vol. 41, No. 11.

Jungkind, Molecular Testing for Infectious Disease, Science, Nov. 16, 2001, p. 1553-1555 vol. 294.

Markoulatos, et al., Laboratory Diagnosis of Common Herpesvirus Infections of the Central Nervous System by a Multiplex PCR Assay, Journal of Clinical Microbiology, Dec. 2001, p. 4426-4432 vol. 39, No. 12.

* cited by examiner

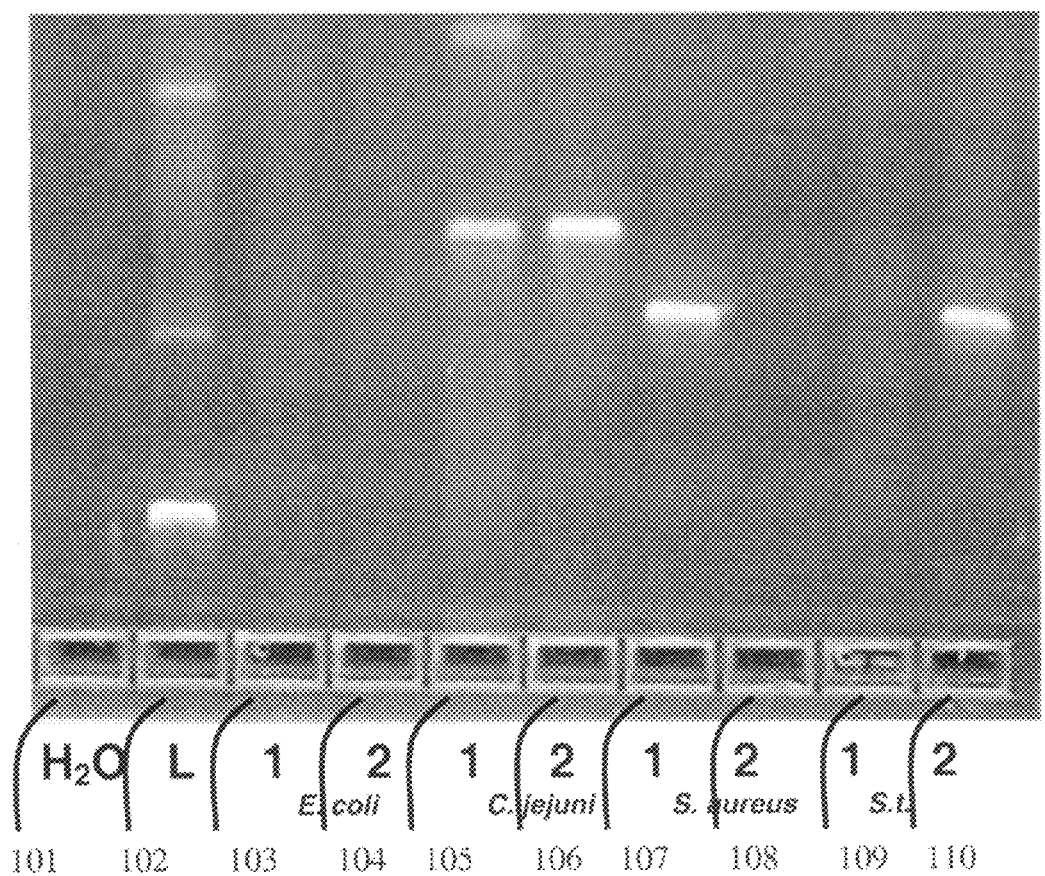

DIFFERENTIAL MULTIPLEXING WITH PATTERN RECOGNITION

RELATED APPLICATION, AND RIGHTS OF THE GOVERNMENT

This application claims the benefit under 35 U.S.C. §119 (e) of provisional Patent Application Ser. No. 60/792,804, filed Apr. 18, 2006, the entire text of which is incorporated herein by reference. The invention described herein may be manufactured and used by or for the Government of the United States for all governmental purposes without the payment of any royalty.

BACKGROUND OF THE INVENTION

The invention relates to assays and more particularly to screening biological samples for a variety of targets.

For example, polymerase chain reaction (PCR) is a powerful molecular technique that allows one to amplify a particular segment of DNA. This technique has been applied to many areas of molecular diagnostics, including the identification of unknown organisms. While PCR traditionally only allowed amplification of a single target, multiplexing allows amplification of several targets in a single reaction mix. Real-time PCR multiplex assays have been commonly employed to screen biological samples for a variety of targets, such as pathogenic bacteria, with considerable research focusing on differentiating potential targets using multicolored fluorophores. What is needed is a simpler method for identifying targets, using only one reporter, and with minimal reagents and supplies.

SUMMARY OF THE INVENTION

This novel form of multiplexing allows the user to probe for multiple targets and simultaneously identify a specific target. An example of solutions provided here comprises: providing one or more assay mixes for a number of targets (the number of assay mixes is less than the number of targets); providing a number of reference patterns (each of the reference patterns is associated with one of the targets); contacting each of a number of aliquots with one of the assay mixes; generating a result pattern, based on positive or negative results; and selecting the reference pattern most similar to the result pattern, to thereby detect the target.

Solutions provided here, which we term differential multiplexing with pattern recognition, may involve molecular or immunological techniques to identify one of many indicators of drug use, illness, disease, or medical condition. For example, we provide a simple method for identifying targets using combinations of real-time PCR reagent mixes and only one reporter. This is an effective and inexpensive method that can be used to identify targets with minimal reagents and supplies.

BRIEF DESCRIPTION OF THE DRAWINGS

FIG. 1 is a photograph of an electrophoresis gel illustrating results of a proof-of-concept experiment.

DETAILED DESCRIPTION

This novel form of multiplexing allows the user to probe for multiple targets and simultaneously identify one or more specific targets using the following general equation: $2^x - 1 = y$, in which x is the number of assay mixes and y is the number of targets identified by the assay mixes. The number of target-specific reagents per assay mix may be characterized by the following equation: $2^{(x-1)}$, in which x is the number of assay mixes. We believe this method will cut costs, effort, and greatly increase efficiency in identification of targets of interest.

Considering PCR for example, differential multiplexing uses a combination of PCR reagent cocktails with mixtures of primers specific to more than one target. Then, using a series of positive/negative reactions and pattern recognition, we are able to identify a specific target. There are far-reaching potential applications in molecular and immuno (antigen-antibody) diagnostics. Real-time PCR may be utilized to eliminate the need for gel electrophoresis (seen in FIG. 1). We provide an effective and inexpensive method that can be used to identify targets with minimal reagents and supplies.

For example, two PCR mixes (assay mixes) will correctly identify each of three target organisms. Assay mix #1 contains PCR components needed to identify organism A and organism B, while assay mix #2 contains PCR components needed to identify organism A and organism C. Patterns for recognition (reference patterns) are as follows in Table 1, where +=positive and 0=negative.

TABLE 1

Patterns for recognition (three targets).

| Target | Mix#1 | Mix#2 |
|---|---|---|
| A | + | + |
| B | + | 0 |
| C | 0 | + |

Other examples are shown in Tables 2-4.

TABLE 2

Patterns for recognition (7 targets).

| | mix 1 | mix 2 | mix 3 | Target Identified |
|---|---|---|---|---|
| Three mixes | + | + | + | 1 |
| can ID seven | + | + | o | 2 |
| targets | + | o | + | 3 |
| | + | o | o | 4 |
| | o | + | + | 5 |
| | o | + | o | 6 |
| | o | o | + | 7 |
| Reagents in mix | 1, 2, 3, 4(4) | 1, 2, 5, 6(4) | 1, 3, 5, 7(4) | |

TABLE 3

Patterns for recognition (15 targets).

| | mix 1 | mix 2 | mix 3 | mix 4 | Target Identified |
|---|---|---|---|---|---|
| Four mixes | + | + | + | + | 1 |
| can ID 15 | + | + | + | o | 2 |
| targets | + | + | o | o | 3 |
| | + | + | o | + | 4 |
| | + | o | + | + | 5 |
| | + | o | o | + | 6 |
| | + | o | + | o | 7 |
| | + | o | o | o | 8 |
| | o | + | + | + | 9 |
| | o | + | + | o | 10 |
| | o | + | o | o | 11 |
| | o | + | o | + | 12 |

TABLE 3-continued

Patterns for recognition (15 targets).

|  | mix 1 | mix 2 | mix 3 | mix 4 | Target Identified |
|---|---|---|---|---|---|
|  | o | o | + | + | 13 |
|  | o | o | o | + | 14 |
|  | o | o | + | o | 15 |
| Reagents in mix | 1, 2, 3, 4, 5, 6, 7, 8(8) | 1, 2, 3, 4, 9, 10, 11, 12(8) | 1, 2, 5, 7, 9, 10, 13, 15(8) | 1, 4, 5, 6, 9, 12, 13, 14(8) |  |

TABLE 4

Patterns for recognition (31 targets).

|  | mix 1 | mix 2 | mix 3 | mix 4 | mix 5 | Target Identified |
|---|---|---|---|---|---|---|
| Five mixes can ID 31 targets | + | + | + | + | + | 1 |
|  | + | + | + | + | o | 2 |
|  | + | + | + | o | o | 3 |
|  | + | + | + | o | + | 4 |
|  | + | + | o | + | + | 5 |
|  | + | + | o | o | + | 6 |
|  | + | + | o | + | o | 7 |
|  | + | + | o | o | o | 8 |
|  | + | o | + | + | + | 9 |
|  | + | o | + | + | o | 10 |
|  | + | o | + | o | o | 11 |
|  | + | o | + | o | + | 12 |
|  | + | o | o | + | + | 13 |
|  | + | o | o | o | + | 14 |
|  | + | o | o | + | o | 15 |
|  | + | o | o | o | o | 16 |
|  | o | + | + | + | + | 17 |
|  | o | + | + | + | o | 18 |
|  | o | + | + | o | o | 19 |
|  | o | + | + | o | + | 20 |
|  | o | + | o | + | + | 21 |
|  | o | + | o | o | + | 22 |
|  | o | + | o | + | o | 23 |
|  | o | + | o | o | o | 24 |
|  | o | o | + | + | + | 25 |
|  | o | o | + | + | o | 26 |
|  | o | o | + | o | o | 27 |
|  | o | o | + | o | + | 28 |
|  | o | o | o | + | + | 29 |
|  | o | o | o | o | + | 30 |
|  | o | o | o | + | o | 31 |
| reagents in mix | 1, 2, 3, 4, 5, 6, 7, 8, 9, 10, 11, 12, 13, 14, 15, 16(16) | 1, 2, 3, 4, 5, 6, 7, 8, 17, 18, 19, 20, 21, 22, 23, 24(16) | 1, 2, 3, 4, 5, 9, 10, 11, 12, 17, 18, 19, 20, 25, 26, 27, 28(16) | 1, 2, 5, 7, 9, 10, 13, 15, 17, 18, 21, 2325, 26, 29, 31(16) | 1, 4, 5, 6, 9, 12, 13, 14, 17, 20, 21, 22, 25, 28, 29, 30(16) |  |

Differential Multiplex PCR has direct application to rapid identification of biowarfare agents (BWA) and pathogens of military significance. Properly formulated, the quantity of reagents needed to identify BWA and/or other pathogens of military significance can be significantly reduced along with a corresponding reduction in cost, time and supplies needed for identification. Identification can be accomplished using a single fluorescent reporter in a manner not previously reported in scientific literature.

This invention has numerous potential commercial uses. It is easily applied to clinical/environmental diagnostics that employ ligand/antiligand binding reactions where pairs of substances (i.e. the binding pairs or ligand/antiligands) bind to each other without binding to other substances, and are visualized using only one reporter. These include molecular (traditional PCR/real-time PCR/reverse transcriptase PCR) or immunological (antibody-based diagnostics) techniques used to identify one of many targets: indicators of drug use, illness, disease, or medical condition. Targets may be chemicals, biologicals, bacteria, viruses, nucleic acids, antigens, antibodies, proteins or metabolites. For example, targets may be cDNA, with a method comprising the steps of isolating RNA from a biological sample; and creating cDNA from the isolated RNA. Considering PCR for example, this invention combines the ability of multiplex PCR to identify several potential targets in a single assay with the use of differential reagent mixes. Ultimately, the application of this invention saves time, effort, consumables, and money. Using this method, significant cost savings will be realized, ranging between 33% (2 mixes/3 targets) and 84% (5 mixes/31 targets) of the original requirement. See Table 5.

TABLE 5

| # of separate multiplex mixes | Number of target-specific reagents/mix | Number of targets identified | Amount of reagent per target |
|---|---|---|---|
| 1 | 1 | 1 | 100% |
| 2 | 2 | 3 | 67% |
| 3 | 4 | 7 | 43% |
| 4 | 8 | 15 | 27% |
| 5 | 16 | 31 | 16% |

PROOF-OF-CONCEPT EXAMPLE: FIG. 1 is a photograph of an electrophoresis gel illustrating results of a proof-of-concept experiment. The goal of this experiment was to identify any one of three potential targets using only two reaction mixes. This was accomplished by creating two combinations of reagent cocktails that would give a predictable pattern of results specific to each target. Our preliminary results demonstrated that each target can be identified using this method. These data indicate that the identification of 5 nucleic acid targets can be simplified and made more cost effective by employing differential multiplexing with pattern recognition.

Our experiment involved positive identification of *Campylobacter jejuni*, *Salmonella typhimurium*, and *Staphylococcus aureus* by differential multiplexing using only two assays. We Purchased/optimized DNA primers for *Salmonella typhimurium*, *Staphylococcus aureus*, and *Campylobacter jejuni*. These primers were described in H. Fukushima, et al., "Duplex Real-Time SYBR Green PCR Assays for Detection of 17 Species of Food- or Waterborne Pathogens in Stools," Journal Of Clinical Microbiology, November 2003, Vol. 41, p. 5134-5146 (hereby incorporated by reference).

We cultured bacteria (*Salmonella typhimurium*, *Staphylococcus aureus*, *Campylobacter jejuni*, and *Escherichia coli*) and extracted DNA using PrepMan® Ultra (Applied Biosystems®, LLC).

We performed PCR on a military Ruggedized Advanced Pathogen Identification Device (Idaho Technology, Inc) as follows: PCR mastermix was prepared using Ready-to-Go® PCR beads, (GE Healthcare, formerly Pharmacia® Biotech, Inc.) (see next table).

Upon completion of PCR, the amplicon was visualized by electrophoresis using a 4% agarose E-Gel® (Invitrogen® Corp).

As seen in FIG. 1, *C. jejuni*, *S. aureus*, and *Salmonella* produced distinct patterns, enabling definitive identification. Lane 101 contained water. Lane 102 contained a ladder, a mixture of DNA fragments of known size. Lane 103 contained *Escherichia coli* amplicon with Mix #1. Lane 104 contained *Escherichia coli* amplicon with Mix #2. Lane 105 contained *Campylobacter jejuni* amplicon with Mix #1. Lane 106 contained *Campylobacter jejuni* amplicon with Mix #2. Lane 107 contained *Staphylococcus aureus* amplicon with Mix #1. Lane 108 contained *Staphylococcus aureus* amplicon with Mix #2. Lane 109 contained *Salmonella typhimurium* amplicon with Mix #1. Lane 110 contained *Salmonella typhimurium* amplicon with Mix #2. Comparing FIG. 1 (result pattern) with Table 7 (Reference Patterns), Lanes 105-106 correspond to the predicted pattern for *Campylobacter jejuni* (++). Lanes 107-108 correspond to the predicted pattern for *Staphylococcus aureus* (+0). Lanes 109-110 correspond to the predicted pattern for *Salmonella typhimurium* (0+).

We have demonstrated the proof of concept that three nucleic targets can be individually identified using PCR and only two combinations of multiplex cocktails. Employment of this technique reduced the level of effort, reagents, consumables, and cost per test by one third.

TABLE 6

Materials and Methods (Mastermix)

| Tube # | Ready To Go Bead | Campylobacter jejuni primers (0.5 uM) | Staphylococcus aureus primers (0.5 uM) | Salmonella typhimurium primers (0.5 uM) | DNA (0.5 ng/uL) | H2O |
|---|---|---|---|---|---|---|
| 1a | Yes | 10 uL | 10uL | — | E. coli (Neg) 2 uL | 3 uL |
| 2a | Yes | 10 uL | — | 10 uL | E. coli 2 uL | 3 uL |
| 1b | Yes | 10 uL | 10 uL | — | C. jejuni 2 uL | 3 uL |
| 2b | Yes | 10 uL | — | 10 uL | C. jejuni 2 uL | 3 uL |
| 3a | Yes | 10 uL | 10 uL | — | S. aureus 2 uL | 3 uL |
| 3b | Yes | 10 uL | — | 10 uL | S. aureus 2 uL | 3 uL |
| 4a | Yes | 10 uL | 10 uL | — | Salmonella 2 uL | 3 uL |
| 4b | Yes | 10 uL | — | 10 uL | Salmonella 2 uL | 3 uL |

Cycling conditions were: Hot start×5 min @ 95° C. 45 cycles (1 min @ 95° C., 20 sec @ 60° C., 1 min @ 72° C.).

TABLE 7

Predicted Patterns for Targets of Interest (Reference Patterns).

| Target | Mix#1* | Mix#2** |
|---|---|---|
| A (*C. jejuni*) | + | + |
| B (*S. aureus*) | + | 0 |
| C (*S. typhimurium*) | 0 | + |

*Mix#1 contains probes for target A and B
**Mix#2 contains probes for target A and C

We claim:

1. A method of screening, said method comprising:

providing a plurality of assay mixes for detection of a plurality of targets according to the general equation $2^x - 1 = y$, wherein x is the number of said assay mixes and y is the number of said targets identified by said assay mixes, x being less than y and $x \geq 3$, and wherein each of said assay mixes contains a plurality of target-specific reagents that are capable of detecting a fraction of said targets, at least one of said targets being detected by two or more of said assay mixes, wherein each assay mix contains $2^{(x-1)}$ target-specific reagents;

providing a plurality of reference patterns, wherein each of said reference patterns is associated with one of said targets;

preparing a plurality of aliquots from a sample, wherein the number of said aliquots equals the number of said assay mixes;

contacting each of said aliquots with one of said assay mixes;

generating a result pattern, based on said contacting;

comparing said result pattern with said reference patterns; and determining, based on said comparing, whether one of said targets is present in said sample.

2. The method of claim 1 wherein said target-specific reagents produce a visual indication of the presence of one or more of said targets when said assay mixes are contacted with said aliquots.

3. The method of claim 2 wherein the visual indication produced by each of said target-specific reagents is different.

4. The method of claim 1 wherein said targets are chemicals.

5. The method of claim 1 wherein said targets are biologicals.

6. The method of claim 5 wherein said targets are bacteria, viruses, nucleic acids, antigens, antibodies, proteins or metabolites.

7. The method of claim 6 wherein said targets are *Campylobacter jejuni*, *Salmonella typhimurium* and *Staphylococcus aureus*.

8. The method of claim 5 wherein said targets are nucleic acids.

9. The method of claim 8 wherein said targets are cDNA.

10. The method of claim 8 further comprising the steps of isolating RNA from a biological sample; and creating cDNA from the isolated RNA.

11. The method of claim 8 wherein said target-specific reagents are primers such that each of said target-specific reagents is a primer specific for a specific nucleic acid.

12. The method of claim 11 wherein each of said target-specific reagents is a pair of primers specific for a specific nucleic acid.

13. The method of claim 11 wherein said target-specific reagents are oligonucleotide primers such that each of said target-specific reagents is an oligonucleotide primer specific for specific cDNA.

14. The method of claim 5 wherein said target-specific reagents are antibodies, wherein each antibody is specific to a specific target.

15. The method of claim 14 wherein the specific targets are proteins.

16. The method of claim 14 wherein the specific targets are metabolites.

17. The method of claim 1 further comprising
generating a result pattern, based on said contacting and based on positive or negative results; and selecting one of said reference patterns that is most similar to said result pattern to thereby detect which of said targets is associated with said selected reference pattern.

* * * * *